United States Patent [19]

Hofmann

[11] Patent Number: 4,941,068
[45] Date of Patent: Jul. 10, 1990

[54] PORTABLE ION GENERATOR

[75] Inventor: Manfred Hofmann, Bayreuth, Fed. Rep. of Germany

[73] Assignee: Hofmann & Voelkel GmbH, Bayreuth, Fed. Rep. of Germany

[21] Appl. No.: 226,750

[22] Filed: Aug. 1, 1988

[30] Foreign Application Priority Data

Mar. 10, 1988 [DE] Fed. Rep. of Germany ....... 3807940

[51] Int. Cl.$^5$ .................... H01T 23/00; A61N 1/44
[52] U.S. Cl. .................................. 361/231; 361/232; 128/202.25
[58] Field of Search ............... 361/229, 232, 212; 128/202.25, 419 R; 55/103, 130, 146, 148, 152

[56] References Cited

U.S. PATENT DOCUMENTS

| | | | |
|---|---|---|---|
| 3,096,762 | 7/1963 | Winchell | 128/202.25 |
| 4,173,229 | 11/1979 | Haifon | 128/419 R |
| 4,713,724 | 12/1987 | Voelkel | 361/231 |

FOREIGN PATENT DOCUMENTS 0209706 1/1987 PCT Int'l Appl. ............ 128/202.25

Primary Examiner—Brian W. Brown
Attorney, Agent, or Firm—Robert J. Schaap

[57] ABSTRACT

A portable ion generator has a housing with a high tension source therein. The high tension source has two output connections of which one is electrically conductively connected to a high voltage needle electrode while the other is electrically conductively connected to a counterelectrode disposed around the needle electrode. So that the housing of the generator can be worn without being obtrusively visible, without adversely affecting operation of the electrodes, the needle electrode and the counterelectrode are carried by a relatively small carrier member and connected to the high tension source by means of flexible electrical conductor elements. The ion generator has a contact element which is at the potential of the counterelectrode and which may be provided on the housing and/or the carrier member.

28 Claims, 1 Drawing Sheet

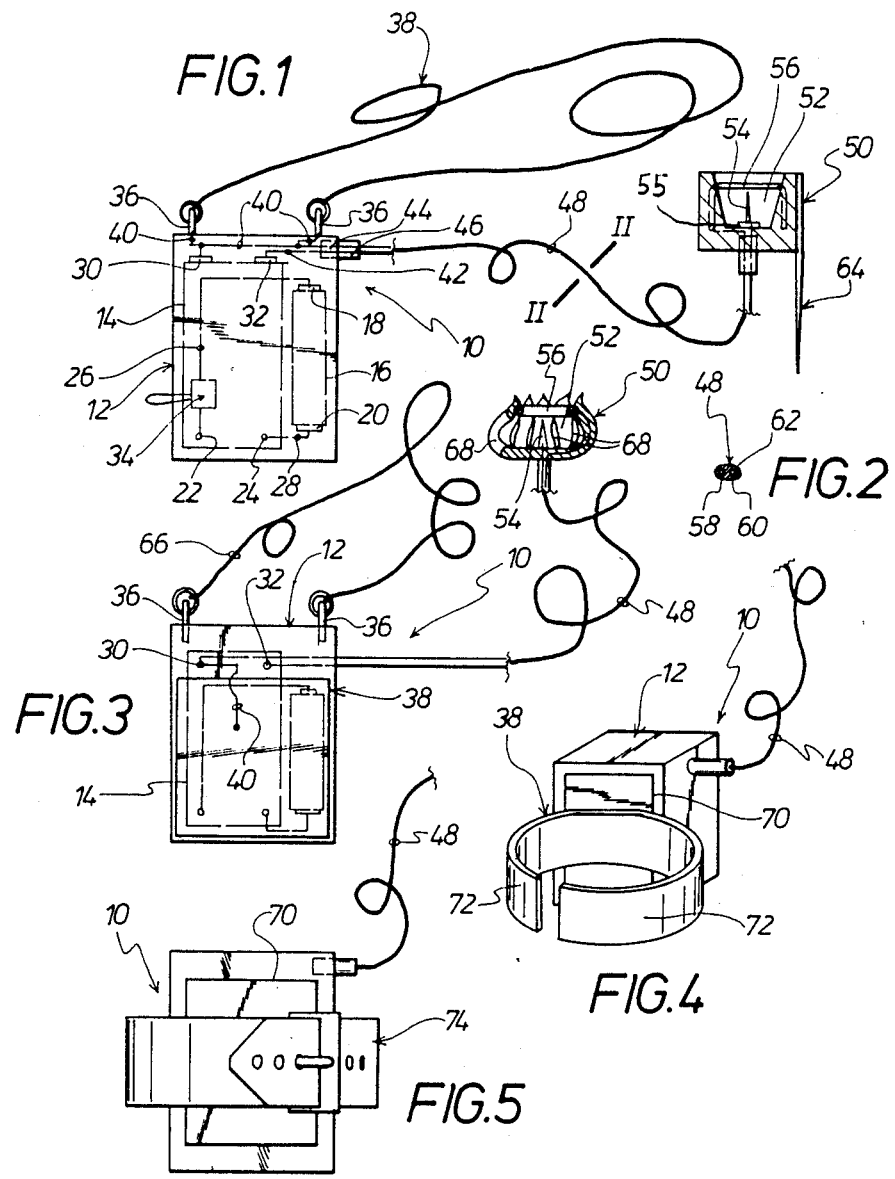

PORTABLE ION GENERATOR

BACKGROUND OF THE INVENTION

In one form of a portable ion generator, as disclosed in European No. 0 209 706 Al, the generator comprises a high tension source which is disposed in a housing and which has first and second connections. The first connection is connected to a high tension needle electrode while the second connection is connected to a counterelectrode disposed at a spacing from the needle electrode. The counterelectrode is electrically conductively connected to a contact element of electrically conductive material. The needle electrode and the counterelectrode are both carried by the housing of the ion generator while the contact element thereof is arranged on the outside of the housing and is for example in the form of a band or chain so that the ion generator can be worn around the neck of a person using same. As the needle electrode and the counterelectrode are intended to be disposed at a position which is accessible more particularly in relation to the nostrils of the person using the ion generator, in order for the generator to be properly effective, that necessarily means that the generator and more specifically the housing thereof is clearly visible since it is worn around the neck and must enjoy free access to the nostril area of the wearer. It is clear however that having the generator in full view in that way is generally unsatisfactory and unacceptable.

Swiss patent specification No. 624 302 discloses an apparatus for producing a dc voltage field in the body of a person wearing the apparatus. That apparatus is not intended to provide for ionisation of particles which are present in the ambient air around the wearer and which may possibly give rise to allergic reactions, but it is intended to produce a dc voltage field in the human body so that a corresponding electrical current flows therein. That arrangement is also worn for example by means of a neck chain or a neck band. As that apparatus is not concerned with particle ionisation, it is clearly possible for it to be worn under clothing so that it is in no way visible from the outside.

U.S. Pat. specification No. 4 173 229 discloses an apparatus which can be worn on the body of a person for example by means of a neck chain, a bracelet or by means of clip elements. As in the case of the above-discussed apparatus of Swiss No. 624 302, the apparatus disclosed in U.S. Pat. No. 4 173 229 is intended to cause an electrical current to flow in the body of the wearer, which is intended to enhance the well-being of that person.

SUMMARY OF THE INVENTION

An object of the present invention is to provide a portable ion generator which can be worn by a person without the generator being clearly visible.

Another object of the invention is to provide a portable ion generator which can be worn in a non-obtrusive fashion without adversely affecting operation thereof for the ionisation of particles likely to trigger allergic reaction.

Yet another object of the present invention is to provide a portable ion generator which is able to produce particle ionisation in the close proximity of the respiratory organs of the person using the generator.

In accordance with the invention, these and other objects are achieved by a portable ion generator comprising a housing and a high tension source disposed in the housing and having first and second connections. A high tension needle electrode is connected to the first connection of the high tension source and a counterelectrode is disposed at a spacing from the needle electrode and is connected to the second connection of the high tension source. A contact element of electrically conductive material is electrically conductively connected to the counterelectrode. The needle electrode and the counterelectrode are carried by a member which is separated in space from the housing, electrical conductor elements providing the connection between the needle electrode and the counterelectrode carried by that member, and the first and second connections respectively of the high tension source.

The electrical conductor elements which connect the carrier member with the electrodes to the housing of the ion generator and thus to the high tension source therein are preferably flexible lines which are electrically insulated from each other. It will be apparent that with that design of generator it is possible for the housing which contains the high tension source to be carried in a generally invisible and unobtrusive fashion on the body or under clothing, with only the carrier member with the electrodes being worn at such a location that the electrodes are not too far away from the respiratory organs. So that the carrier member with the electrodes can also be worn in an unobtrusive fashion, in a preferred feature the carrier member may be in the form of an ornamental or decorative member which has a suitable fixing element. The ornamental or decorative member may be for example an article in the manner of a pin or badge, a jewellery brooch or any other item of jewellery which can be worn at a suitable location. It will be appreciated that it is also possible for the carrier member to be for example similar to a lapel microphone or the like. At any event the configuration of the generator according to the invention provides a comparatively small carrier member which is separate from the housing of the generator and which therefore can be relatively small because it only has to accommodate the high tension needle electrode and the counterelectrode.

The contact element of electrically conductive material, which is disposed on the outside of the housing of the generator, may be a flexible member such as a flexible chain or flexible band or strip. Such an ion generator can be worn by suspending it around the neck by means of the flexible member forming the contact element so that the surface of the skin of the wearer of the generator is at the same potential as the counterelectrode. The housing of the generator can still be worn under clothing so that it is still not visible from the outside.

In another feature of the invention the contact element which is disposed on the outside of the housing of the generator is a flat element which at least partially covers over the outside surface of the housing. The flat element may form a part of the housing or the entire housing itself, in which case it will be appreciated that the two electrical conductor elements between the housing and the carrier member carrying the electrodes are electrically insulated relative to the contact element. The one electrical conductor element which is connected to the counterelectrode may be directly contacted with the flat element of electrically conductive material.

In another preferred feature of the invention, the contact element may be provided with a fixing clamp or clip. In that case the contact element may be worn for example on a wrist, so that in that case the housing of the ion generator which includes the high tension source is worn on the wrist, with the contact element in contact with the surface of the skin at that location. However the contact element may also be provided with a fixing band which may itself comprise electrically conductive material in order to provide electrical contact in the manner of a wristwatch bracelet between the surface of the skin and the band fonning the contact element. However, the fixing band may also consist of an electrically insulating material, for example being made of leather or the like, the only important consideration in that respect being that the contact element which is disposed on the housing of the generator is in contact with the surface of the skin of the user of the device. A similar consideration also applies in regard to the fixing clamp which was referred to hereinbefore. The fixing clamp may also consist of electrically insulating material, provided that the contact element of the generator is in contact with the skin of the user. In that case, irrespective of the particular configuration of the ion generator, the skin of the user thereof is at the same electrical potential as the counterelectrode so that any ionised particles or electrons which originate from the high tension needle electrode are attracted to the surface of the skin of the user of the generator. That ensures that the major part of the ionised particles cannot pass into the mouth or the nostrils of the user, where they could trigger off allergic reactions.

The second electrical conductor element which connects the counterelectrode to the high tension source may be bare of electrical insulation at least along a part of its length between the counterelectrode and the second connection of the high tension source. That can provide for an electrical contact between the second electrical conductor element and the surface of the skin of the wearer of the device, so that once again the skin surface is of the same polarity as the counterelectrode. The first and second electrical conductor elements may form a combined connecting element between the housing and the carrier member carrying the electrodes, and the connector element may be in the form of a neck chain or band. It should be noted however that it is also possible for only the second electrical conductor element to be in the form of a chain or band, while the first electrical conductor element which is connected to the needle electrode is separated from the second electrical conductor element, between the housing of the generator and the carrier member carrying the electrodes.

It will have been seen that, in the forms of the ion generator described above, the contact element may be provided on the housing which accommodates the high tension source. It is also possible however for the contact element not to be provided on the housing but on the carrier member which is separate from the housing and which carries the electrodes. In that case the carrier member must be brought into contact by means of its contact element with the surface of the skin of the user of the ion generator in order to cause the generator to be operative. In accordance with a feature of the invention, that may be achieved for example by the carrier member being disposed on a chain or a bracelet. In an ion generator of that configuration, the contact element may be disposed on the outside of the carrier member and may be for example in the form of a flat element which can be provided on the outside of the carrier member which is of electrically insulating material. It is also possible however for the carrier member to be of electrically conductive material, with the high tension needle electrode being arranged in an electrically insulated condition thereon. When using a carrier member of that nature, it is advantageously possible for the counterelectrode to be integrated in one piece into the carrier member which is of electrically conductive material. That provides a simple ion generator structure because there is no need to produce a separate counterelectrode and fit it into the carrier member.

The housing of the ion generator may he provided with a suitable fixing means which may be for example a fixing clip, a clamp arrangement or the like. The fixing means may comprise electrically conductive material or electrically insulating material. It may be provided on a housing which may or may not carry a contact element, as referred to above.

Further objects, features and advantages of the present invention will be apparent from the following description of preferred embodiments of the portable ion generator according to the invention.

BRIEF DESCRIPTION OF THE DRAWING

FIG. 1 shows a first embodiment of the portable ion generator according to the invention, with a neck chain of electrically conductive material which is electrically conductively connected to a connection of the high tension source of the generator, FIG. 2 is a view in section taken along line II—II through the connecting member of the FIG. 1 generator, which electrically conductively connects the housing of the FIG. 1 generator to the carrier member carrying the electrodes of the generator, FIG. 3 shows another embodiment of the portable ion generator which differs from the FIG. 1 generator in that the neck chain on the housing thereof is not electrically conductively connected to the high tension source, FIG. 4 is a perspective view showing part of a third embodiment of the ion generator, without illustrating the carrier member carrying the electrodes of the generator, and FIG. 5 is a sideview of part of a fourth embodiment of the portable ion generator, without illustrating the carrier member carrying the electrodes of the generator.

DESCRIPTION OF THE PREFERRED EMBODIMENTS

Referring firstly to FIG. 1, shown therein is a portable ion generator 10 comprising a housing indicated generally at 12, which accommodates a high tension source 14 and a power source 16, illustrated in the form of a small battery, with first and second connections indicated respectively at 18 and 20. The connections 18 and 20 are electrically conductively connected to input connections or terminals 22 and 24 of the high tension source 14. The electrically conductive connection between the connections 18 and 20 and the connections 22 and 24 is made by suitable connecting lines 26 and 28 indicated diagrammatically in FIG. 1 by the broken line representations thereof.

Besides the input connections 22 and 24, the high tension source 14 also has first and second output connections or terminals 30 and 32 across which there is a high tension with very low current strength when the portable ion generator 10 :e switched on. The ion generator. 10 has an on-off switch 34 which in the illustrated embodiment is connected into the connecting line 26.

The housing 12 of the ion generator 10 has two fixing eyes 36 which consist of an electrically conductive material. The first and second ends of a contact element 38 are secured to respective ones of the two fixing eyes 36. In the embodiment illustrated in FIG. 1, the contact element 38 is in the form of a flexible member of electrically conductive material such as a neck chain or a neck band. The two ends of the contact element 38 are electrically conductively connected to the one output connection 30 of the high tension source 14, as diagrammatically indicated by a connecting line 40 in FIG. 1. The other output connection 32 of the high tension source 14 is in contact with a connecting line 42. The connecting lines 40 and 42 pass into a plug socket 44 provided in the housing 12 of the ion generator 10. The connecting lines 40 and 42 are electrically insulated from each other.

Fitted into the socket 44 is a plug or jack 46 which is disposed at one end of a flexible connecting element 48. Carried at the other second end of the connecting element 48 is a carrier member 50 which has a recess 52 therein. Disposed in the recess 52 is a high tension electrode 54 in the form of a needle electrode, and a counterelectrode 56 which is disposed in concentric relationship around the high tension needle electrode 54. The needle electrode 54 may be insulated from the carrier member 50 by means of an electrically insulating mounting element 55.

It will be appreciated that FIG. 1 only shows the connecting element 48 in the form of a simple winding line, for the purposes of simplifying the drawing. Reference will therefore now be made to FIG. 2 which shows that the flexible connecting element 48 comprises first and second electrical lines 58 and 60 which are electrically separated from each other by electrical insulation 62. For example the high tension needle electrode 54 is electrically conductively connected to the one output connection 32 of the high tension source 14 by way of the electrical conductor element 58. The conductor element 58 would extend through the mounting element 55 and connect to the needle electrode 54. The counterelectrode 56 is then electrically conductively connected to the other output connection 30 of the high tension source 14, by means of the second electrical conductor element 60.

At the same time the flexible contact element 38 is electrically conductively connected to the counterelectrode 56 so that the contact element 38 and the counterelectrode 56 are of the same polarity and potential.

Referring again to FIG. 1, it will be seen therefrom that the carrier member 50 has a fixing element 64 for fixing the carrier member for example to an article of clothing of the person using the ion generator, being illustrated in the form of a fixing pin. However the fixing element 64 may also be in the form of a clip or clamping means or the like.

Reference will now be made to FIG. 3 showing a second embodiment of the portable ion generator 10 which differs from the structure shown in FIG. 1 more specifically in that the fixing eyes 36 are not electrically conductively connected to the one output connection 30 of the high tension source 14. On the contrary, in the FIG. 3 embodiment, the eyes 36 are electrically insulated in the housing 12 of the ion generator 10. A flexible neck band as indicated at 66 is secured by means of its respective end portions to the fixing eyes 36. The neck band 66 may comprise any suitable material. It does not have to be of electrically conducting material but may also be a band of material or the like which has electrically insulating properties. In this embodiment of the ion generator 10, the contact element 38 is in the form of a flat element consisting of an electrically conductive material. The flat element 38 covers at least a part of the outside surface of the housing 12 of the ion generator 10. In use of the portable ion generator therefore the housing 12 is worn against the skin of the user thereof in such a way that the flat contact element 38 is in contact with the skin of the user. The skin of the user is thus at the same potential as the flat contact element 38 which is electrically conductively connected to the output connection 30. The electrically conductive connection between the output connection 30 of the high tension source 14 and the contact element 38 is diagrammatically indicated in FIG. 3 by a line representing the connecting line 40.

The ion generator shown in FIG. 3 also comprises a carrier member 50 for carrying the electrodes, in the form of a decorative or ornamental member. The carrier member 50 is again connected to the housing 12 of the generator 10 by means of a flexible connecting element 48. The carrier member 50 which may be for example in the form of a flower head or bulb has a recess 52 which accommodates a high tension needle electrode 54 and a counterelectrode 56 disposed substantially concentrically therearound. The carrier member 50 has lateral openings 68 through which air can flow into the central recess 52 from outside the carrier member 50. In that way, electrons issuing from the high tension needle electrode 54 can be dispersed with that air into the atmosphere around the carrier member 50.

Like the connecting element 48 diagrammatically indicated in FIG. 1, the connecting element 48 in FIG. 3 comprises two electrical conductor elements 58 and 60, as shown in FIG. 2. The high tension needle electrode 54 is connected to the one output connection 32 of the high tension source 14 by means of the one conductor element 58 while the counterelectrode 56 is electrically conductively connected to the other output connection 30 of the high tension source 14 by way of the second electrical conductor element 60. In other respects the portable ion generator 10 shown in FIG. 3 substantially corresponds to that shown in FIG. 1, so that reference may be made to the FIG. 1 description for further details and features of the FIG. 3 structure. It will be appreciated that, although FIG. 3 does not show an on-off switch as indicated at 34 in FIG. 1, the FIG. 3 structure will usually incorporate a suitable control unit of that nature.

Reference is now made to FIG. 4 showing a third embodiment of the portable ion generator 10 without however illustrating the carrier member indicated at 50 in FIGS. 1 and 2 for carrying the electrodes 54 and 56, with the carrier member 50 being separated in space from the housing 12 of the ion generator 10. FIG. 4 also shows only a part of the connecting element 48 between the carrier member (not shown) and the housing 12 of the ion generator 10, which accommodates the high tension source. In the FIG. 4 construction, the contact element 38 comprises a flat element 70 and fixing clip portions 72 which are of a resilient nature and which are connected to the element 70. In this embodiment the clip portions 72 are of an electrically conductive material but it will be appreciated that it would also be possible for the clip portions 72 to be made from electrically insulating material, in which case skin contact is achieved only by the flat element 70 being applied against the skin of the user of the ion generator 10. An ion generator 10 of that kind may be worn for example in the manner of a wristwatch on the arm or wrist of a user thereof.

FIG. 5 shows another embodiment of the portable ion generator 10 according to the invention, which differs from the ion generator 10 shown in FIG. 4 in that in place of the fixing clip portions 72, the FIG. 5 structure has a fixing band or strap 74. The fixing strap 74 may comprise electrically conductive material and may be electrically conductively connected to the one output connection 30 which is shown in FIGS. 1 and 2 and which is also connected by way of the connecting element 48 to the counterelectrode 56. The fixing strap 74 however may also comprise an electrically non-conductive material such as for example a leather strap or a textile strap or band. In that case the skin contact with the output connection indicated at 30 in FIGS. 1 and 2, which is electrically conductively connected to the counterelectrode 56, is made by way of the flat element 70 which is of electrically conductive material and which in turn is electrically conductively connected to the output connection 30.

Irrespective of the actual configuration of the portable ion generator 10, in the described embodiments the high tension needle electrode 54 and the counterelectrode 56 are separated in space from the housing 12 of the ion generator 10, which accommodates the high tension source 14, and are connected to the housing 12 by way of the connecting element 48. The electrical connection between the two output connections 30 and 32 of the high tension source 14 and the high tension needle electrode 54 and the counterelectrode 56 respectively is made by means of the electrical conductor elements indicated at 58 and 60 in FIG. 2, forming part of the connecting element 48.

The drawings show embodiments of the ion generator in which the contact element 38 is provided on the housing 12 which contains the high tension source 14 but it is also possible for the housing 12 to be made without the contact element, simply from electrically insulating material, with the contact element being provided on the carrier member 50 for the electrodes 54 and 56, which is separated in space from the housing 12. In that case for example the carrier member 50 may comprise electrically insulating material and may carry the contact element of electrically conductive material, on the outside surface of the carrier member. Alternatively it is possible for the carrier member 50 to be made overall of electrically conductive material, with the high tension needle electrode 15 being arranged in an electrically insulated condition in the recess 52 in the carrier member 50. For example the carrier member 50 shown in FIG. 1 or that shown in FIG. 2 may comprise electrically conductive material, in which case one connecting line or conductor element 58 is for example directly connected to the carrier member 50 while the second connecting conductor element 60 is electrically conductively connected to the high tension needle electrode which in turn is electrically insulated from the carrier member 50. When the carrier member 50 comprises electrically conductive material, it is possible to omit a separate counterelectrode 56, in other words, in that case the counterelectrode 56 is formed by the carrier member 50 itself, and is thus integrated thereinto.

In an ion generator in accordance with the invention as described hereinbefore the high tension needle electrode 54 is preferably connected to the negative output connection of the high tension source 14 while the counterelectrode 56 is connected to the positive terminal of the high tension source.

It will be appreciated that the above-described embodiments of the ion generator were only described by way of example of the invention and that various modifications and alterations may be made therein without thereby departing from the spirit and scope of the invention.

I claim:

1. A portable ion generator comprising:
a housing, a high tension source disposed in the housing and having first and second connections;
a carrier member separated in space from said housing, said carrier member being in the form of a decorative or ornamental member being essentially comprised of a fixing element for fastening the carrier member on an article of clothing of the person using the ion generator, a high tension needle electrode carried by said carrier member and a counterelectrode carried by said carrier member and arranged in spaced apart relationship from said high tension needle electrode;
first and second electrical conductor elements respectively connecting said needle electrode and said counterelectrode to said first and second connections of said high tension source; and
a contact element of electrically conductive material electrically conductively connected to said counterelectrode and mechanically connected with the housing.

2. The portable ion generator of claim 1 wherein said carrier member has a recess which accommodates the high tension needle electrode and the counterelectrode is disposed substantially concentrically therearound.

3. The portable ion generator of claim 2 wherein the carrier member has lateral openings through which air can flow into the central recess from outside the carrier member.

4. The portable ion generator of claim 1 in which the carrier member is in the form of a flower head.

5. The portable ion generator of claim 1 in which the carrier member is in the form of a flower bulb.

6. The portable ion generator of claim 1 wherein said carrier member is of electrical conductive material and the counterelectrode is integrated in the carrier member, and wherein the high tension needle electrode is electrically insulated and arranged thereon.

7. The portable ion generator of claim 2 wherein said carrier member is of electrical conductive material and the counterelectrode is integrated in the carrier member and wherein the high tension needle electrode is electrically insulated and arranged thereon.

8. The portable ion generator of claim 1 wherein the contact element is a flexible member to be arranged around the neck of a person using the ion generator.

9. The portable ion generator of claim 1 wherein the contact element is provided with a fixing clamp means.

10. The portable ion generator of claim 1 wherein the contact element is provided with a fixing band.

11. The portable ion generator of claim 1 wherein said second conductor element is bare of electrical insulation at least along a part of its length between said second connection of said high tension source and said counterelectrode.

12. A portable ion generator comprising:
a housing, a high tension source disposed in the housing and having first and second connections;

a carrier member separated in space from said housing, said carrier member being essentially comprised of a fixing element for fastening the carrier member on an article of clothing of the person using the ion generator, a high tension needle electrode and a counterelectrode carried by said carrier member and arranged in spaced apart relationship from said high tension needle electrode;

first and second electrical conductor elements respectively connecting said needle electrode and said counterelectrode to said first and second connections of said high tension source;

a contact element of electrically conductive material which is provided on the outside of and connected to the housing and comprises an element which at least partially covers the outside of the housing and which is conductively connected to said counterelectrode;

and fastening means for carrying the housing such that the element is in contact with the skin of a person using the ion generator.

13. The portable ion generator of claim 12 wherein the carrier member is in the form of a decorative ornamental member.

14. The portable ion generator of claim 12 wherein said carrier member has a recess which accommodates the high tension needle electrode and the counterelectrode is disposed substantially concentrically therearound.

15. The portable ion generator of claim 12 wherein the carrier member has lateral openings through which air can flow into the central recess from outside of the carrier member.

16. The portable ion generator of claim 14 wherein the carrier member has lateral openings through which air can flow into the central recess from outside of the carrier member.

17. The portable ion generator of claim 13 in which the carrier member is in the form of a flower head.

18. The portable ion generator of claim 13 in which the carrier member is in the form of a flower bulb.

19. The portable ion generator of claim 12 wherein said carrier member is of electrical conductive material and the counterelectrode is integrated in the carrier member and wherein the high tension needle electrode is electrically insulated and arranged thereon.

20. A portable ion generator comprising:
a housing, a high tension source disposed in the housing and having first and second connections;
a carrier member separated in space from said housing, a high tension needle electrode being electrically insulated and arranged on the carrier member, said carrier member comprising an electrically conductive material and containing a counterelectrode arranged in spaced apart relationship from said high tension needle electrode, and first and second electrical conductor elements respectively connecting said needle electrode and said counterelectrode to said first and second connections of said high tension source, said needle electrode and said counterelectrode functioning as a spray electrode arrangement which is separate in space from said housing, and
said carrier member with the needle electrode and counterelectrode also operating as a contact element for contacting the body of a person using the ion generator.

21. The ion generator of claim 20 wherein said carrier member has a recess which accommodates the high tension needle electrode and the counterelectrode is disposed substantially concentrically therearound.

22. The ion generator of claim 21 in which the carrier member is constructed with the size and shape of a decorative or ornamental member.

23. A portable ion generator comprising:
a housing, a high tension source disposed in the housing and having first and second connections;
a carrier member which is separated in space from said housing comprising a high tension needle electrode and a counterelectrode in a spaced apart relationship to said high tension needle electrode;
first and second electrical conductor elements respectively connecting said needle electrode and said counterelectrode to said first and second connections of said high tension source;
said second electrical conductor element being bare of insulation at least along a part of its length between said second connection of said high tension source and said counterelectrode and being located to be in contact with and act as a contact element to the skin of a person using the ion generator.

24. The ion generator of claim 23 wherein the carrier member consists essentially of a fastening element for fastening the carrier member to an article of clothing of the person using the ion generator, the high tension needle electrode and the counter electrode.

25. The ion generator of claim 25 wherein the carrier member is a piece of jewelry.

26. A portable ion generator comprising:
a housing, a high tension source disposed in the housing and having first and second connections;
a carrier member separated in space from said housing, a high tension needle electrode being electrically insulated and arranged on the carrier member, said carrier member comprising an electrically conductive material and containing a counterelectrode arranged in spaced apart relationship from said high tension needle electrode, and first and second electrical conductor element respectively connecting said needle electrode and said counterelectrode to said first and second connections of said high tension source, said carrier member also having a fixing element for fastening the carrier member onto an article of clothing of a person using the ion generator, and
a contact element for contacting the body of a person using the ion generator.

27. A portable ion generator comprising:
a housing, a high tension source disposed in the housing and having first and second connections;
a carrier member separated in space from said housing, a high tension needle electrode being electrically insulated and arranged on the carrier member, said carrier member comprising an electrically conductive material and containing a counterelectrode arranged in spaced apart relationship from said high tension needle electrode, and first and second electrical conductor elements respectively connecting said needle electrode and said counterelectrode to said first and second connections of said high tension source, said second conductor element being bare of electrical insulation at least along a portion of its length between the second connection of said high tension source and said counterelectrode, and a contact element for contacting the body of a person using the ion generator.

28. A portable ion generator comprising:

a housing, a high tension source disposed in the housing and having first and second connections;

a carrier member separated in space from said housing, a high tension needle electrode being electrically insulated and arranged on the carrier member, said carrier member comprising an electrically conductive material and containing a counterelectrode arranged in spaced apart relationship from said high tension needle electrode, and first and second electrical conductor elements respectively connecting said needle electrode and said counterelectrode to said first and second connections of said high tension source, said carrier member having lateral openings through which air can flow into a central recess in the carrier member from outside the carrier member, and a contact element for contacting the body of a person using the ion generator.

* * * * *